United States Patent [19]

Schumacher et al.

[11] Patent Number: 5,382,563
[45] Date of Patent: Jan. 17, 1995

[54] HERBICIDAL AGENTS

[75] Inventors: Hans Schumacher, Flösheim am Main; Hans P. Huff, Eppstein/Taunus; Erwin Hacker, Hochheim am Main, all of Germany

[73] Assignee: Hoechst Aktiengesellschaft, Franfurt am Main, Germany

[21] Appl. No.: 531,940

[22] Filed: Jun. 1, 1990

[30] Foreign Application Priority Data

Jun. 5, 1989 [DE] Germany ............................ 3918287

[51] Int. Cl.⁶ .............................................. A01N 43/54
[52] U.S. Cl. ..................................... 504/136; 504/148
[58] Field of Search .................... 71/92, 120; 504/136, 504/148

[56] References Cited

U.S. PATENT DOCUMENTS 2,960,534 11/1960 Scherer et al. .................... 260/553
3,649,241 3/1972 Fitzgerald et al. ................ 71/120
4,601,747 7/1986 Willms et al. ..................... 71/92

FOREIGN PATENT DOCUMENTS 2098901 12/1983 European Pat. Off.
0131258 7/1984 European Pat. Off.

Primary Examiner—Glennon H. Hollrah
Assistant Examiner—Brian M. Burn
Attorney, Agent, or Firm—Curtis, Morris & Safford

[57] ABSTRACT

Combinations consisting of 3-(4,6-dimethoxy-2-pyrimidinyl)-1-[(N-methyl-N-methylsulfonyl)-aminosulfonyl]-urea (I) and a phenylurea (II) are useful herbicides having synergistic properties.

9 Claims, No Drawings

HERBICIDAL AGENTS

The invention relates to herbicidal agents which contain 3-(4,6-dimethoxy-2-pyrimidinyl)-1-[(N-methyl-N-methylsulfonyl)-aminosulfonyl]-urea of the formula

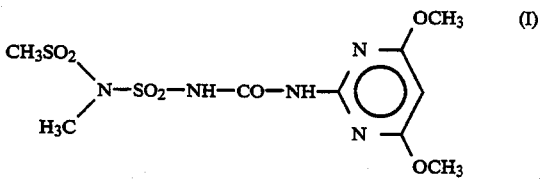

in combination with a herbicide from the class of phenylureas (II). Typical phenylurea derivatives of the formula II are, for example, isoproturon (IIa), monolinuron (IIb), linuron, chlortoluron, diuron, neburon and methabenzthiazuron. They are described without exception in "Pesticide Manual", 7th edition 1983 or 8th edition 1987, The British Crop Protection Council, London. The active compound I is known from EP-A-131,258 (U.S. Pat. No. 4,601,747).

The application also relates to three-component combinations of the active compound I with in each case two phenylurea derivatives. Surprisingly, the active compound combinations claimed have a synergistic activity which was not to be expected on the basis of the action of the individual components.

The active compound combinations according to the invention attack a broad spectrum of annual and perennial weeds. They are suitable, for example, for controlling *Chenopodium album* (white gooseloot), *Sinapis sp.* (charlock), *Stellaria media* (common chickweed), *Capsella bursa pastoris* (shepherd's-purse), *Alopecurus myosuroides* (black-grass), *Apera spica venti* (loose silky-bent) and the like. Because they are harmless to useful plants, they can be used in numerous crops of useful plants, for example by the pre- and post-emergence method in cereals, such as wheat and barley, and by the pre-emergence method in potatoes and maize.

The mixing ratio of the active compounds I and II can vary within wide limits and as a rule is between 1:10 and 1:400. The choice of mixing ratio depends on various parameters, such as, for example, the nature of mixing partner II, the stage of development of the weeds and the weed spectrum. Mixing ratios between 1:20 and 1:300 are preferably chosen. The application amounts of the active compound mixtures according to the invention are as a rule between 0.06 and 4 kg/ha, preferably between 0.1 and 4 kg/ha. The application amounts of the active compound mixtures according to the invention for application in the open are as a rule between 0.4 and 4.0 kg/ha.

The agents according to the invention can be marketed in the customary formulations familiar to the expert, for example as wettable powders, dusting agents, granules, dispersion concentrates, emulsifiable concentrates or solutions for spraying. The formulated agents here in general contain the active compounds in concentrations of 2 to 95% by weight.

These individual types of formulation are known in principle and are described, for example, in: Winnacker-K üchler, "Chemische Technologie (Chemical Technology)", volume 7, C. Hauser Verlag Munich, 4th edition, 1986; van Falkenberg, "Pesticides Formulations", Marcel Dekker N.Y., 2nd edition, 1972-73; K. Martens, "Spray Drying Handbook, 3rd edition, 1979, G. Goodwin Ltd. London.

The formulation auxiliaries needed, such as inert materials, surfactants, solvents and other additives, are likewise known and are described, for example, in: Watkins, "Handbook of Insecticide Dust Diluents and Carriers", 2nd edition, Darland Books, Caldwell N.J.; H. v. Olphen, "Introduction to Clay Colloid Chemistry"; 2nd edition, J. Wiley & Sons, N.Y.; Marschen, "Solvents Guide", 2nd edition, Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Sch önfeldt, "Grenzfl ächenaktive Äthylenoxidaddukte (Surface-active ethylene oxide adducts)", Wiss. Verlagsgesell., Stuttgart 1976; Winnacker-K üchler, "Chemische Technologie (Chemical Technology)", volume 7, C. Hauser Verlag Munich, 4th edition 1986.

On the basis of these formulations, combinations with other substances having a pesticidal action, fertilizers and/or growth regulators can also be prepared, for example in the form of a finished formulation or as a tank mix.

Wettable powders are preparations which are uniformly dispersible in water and which, as well as the active compound and in addition to a diluent or inert substance, also contain wetting agents, for example polyoxyethylated alkylphenols, polyoxyethylated fatty alcohols or polyoxyethylated fatty amines, alkanesulfonates or alkylbenzenesulfonates, and dispersing agents, for example sodium lignin-sulfonate, sodium 2,2'-dinaphthylmethane-6,6'-disulfonate, sodium dinaphthylmethanedisulfonate, sodium dibutylnaphthylsulfonate or sodium oleyl-methyl-taurate.

Emulsifiable concentrates are prepared by dissolving the active compound in an organic solvent, for example butanol, cyclohexanone, dimethylformamide, xylene or higher-boiling aromatics or hydrocarbons, one or more emulsifiers being added. Examples of emulsifiers which can be used are: calcium alkylarylsulfonates, such as Ca dodecylbenzenesulfonate, or nonionic emulsifiers, such as fatty acid polyglycol esters, alkylarylpolyglycol ethers, such as polyoxyethylated alkylphenols, fatty alcohol polyglycol ethers, propylene oxide-ethylene oxide condensation products, alkyl polyethers, polyethoxylated fatty amines, such as polyethoxylated oleyl- or stearylamine, sorbitan fatty acid esters, polyoxyethylene sorbitan fatty acid esters or polyoxyethylene sorbitol esters.

Dusting agents are obtained by grinding the active compound with finely divided solid substances, for example talc or naturally occurring clays, such as kaolin, bentonite, pyrophillite or diatomaceous earth. Soil granules or scattering granules can be prepared either by spraying the active compound onto an absorbent granular inert material or by applying active compound concentrates to the surface of carriers, such as sand or kaolinite, or of a granular inert material by means of adhesives, for example polyvinyl alcohol, sodium polyacrylate or even mineral oils. Suitable active compounds can also be granulated in the manner customary for the preparation of fertilizer granules—if desired as a mixture with fertilizers.

The total active compound concentration in wettable powders varies between about 10% and 95%, the remainder consisting of the formulation additives described above. In emulsifiable concentrates, the active compound concentration is about 10% to 80%. Dust-like formulations usually contain 5% to 20% of active compounds, and sprayable solutions about 2% to 20%. The active compound content in granules depends partly on the form (liquid or solid) in which the active compounds are present and on what granulating auxiliaries, fillers and the like are used.

The content in granules which are dispersible in water is in general between 10 and 90% by weight.

In addition, the active compound formulations mentioned contain, if appropriate, the particular customary adhesives, wetting agents, dispersing agents, emulsifiers, penetration agents, solvents, fillers or carrier substances.

For use, the formulations in the commercially available form are diluted, if appropriate, in the customary manner, for example by means of water in the case of wettable powders, emulsifiable concentrates, dispersions and water-dispersible granules. Dust-like formulations, soil granules and sprinkling granules and sprayable solutions are usually not diluted further with additional inert substances before use.

The combinations according to the invention of the active compounds I and II can be used by the pre-emergence or post-emergence method. The active compounds I and II are applied here individually in succession or together to the plants or their growing area. Use by the post-emergence method is preferred.

The application amount required for the compounds of the formula (I) varies according to the external conditions, such as temperature, humidity, nature of the herbicide used and the like.

Mixtures or mixed formulations with other active compounds, such as, for example, insecticides, acaricides, herbicides, fertilizers, growth regulators or fungicides are possible where appropriate.

The following examples serve to illustrate the invention:

A. Formulation examples a) A dusting agent is obtained by mixing 10 parts by weight of active compound mixture and 90 parts by weight of talc as an inert substance, and comminuting the mixture in an impact mill.

b) A wettable powder which is readily dispersible in water is obtained by mixing 25 parts by weight of active compound mixture, 64 parts by weight of kaolin-containing quartz, as an inert substance, 10 parts by weight of potassium ligin sulfonate and 1 part by weight of sodium oleyl-methyl-taurate, as a wetting and dispersing agent, and grinding the mixture in a pinned disk mill.

c) A dispersion concentrate which is readily dispersible in water is obtained by mixing 20 parts by weight of active compound mixture with 6 parts by weight of alkylphenolpolyglycol ether (®Triton X 207), 3 parts by weight of isotridecanolpolyglycol ether (8 mol of ethylene oxide) and 71 parts by weight of paraffinic mineral oil (boiling range, for example, about 255° to 377° C.) and grinding the mixture to a fineness of less than 5 microns in a ball attrition mill.

d) An emulsifiable concentrate is obtained from 15 parts by weight of active compound mixture, 75 parts by weight of cyclohexanone, as a solvent, and 10 parts by weight of oxyethylated nonylphenol (10 mol of ethylene oxide), as an emulsifier.

e) Water-dispersible granules are obtained by mixing 75 parts by weight of active compound mixture,
10 parts by weight of calcium lignin-sulfonate,
5 parts by weight of sodium lauryl sulfate,
3 parts by weight of polyvinyl alcohol and
7 parts by weight of kaolin, grinding the mixture on a pinned disk mill and granulating the powder in a fluidized bed by spraying on water as the granulate liquid.

f) Water-dispersible granules are also obtained by homogenizing and precomminuting 25 parts by weight of active compound mixture,
5 parts by weight of sodium 2,2'-dinaphthylmethane-6,6'-disulfonate,
2 parts by weight of sodium oleyl-methyl-taurate,
1 part by weight of polyvinyl alcohol,
17 parts by weight of calcium carbonate and
50 parts by weight of water on a colloid mill, subsequently grinding the mixture on a bead mill, atomizing the resulting suspension in a spray tunnel by means of a one-component nozzle and drying the product.

g) Extruded granules are obtained by mixing 20 parts by weight of active compound mixture, 3 parts by weight of sodium lignin-sulfonate, 1 part by weight of carboxymethylcellulose and 76 parts by weight of kaolin, and grinding the mixture and moistening it with water. This mixture is extruded and then dried in a stream of air.

B. Biological examples

In the following use examples, the test plants were grown in pots in a greenhouse.

The concentrates, diluted in water, were applied after the monocotyledonous plants Apera spica venti, Triticum aestivum and Hordeum vulgare had reached the 3-4 leaf stage and the dicotyledonous plants Chenopodium album and Sinapis arvensis had grown to 5-10 cm.

The action (damage) was rated after 4 weeks. The experimental results are shown in the following tables.

Evidence of synergism is obtained by comparing the additive degrees of action calculated from the actions of the individual components with the degree of action of the active compound combination found experimentally.

The additive degree of action is calculated in accordance with the formula of S. R. Colby (cf. Calculating synergistic and antagonistic responses of herbicide combinations, Weeds, 15, 1967, pages 20 to 22).

The formula states $$E = X + Y - \frac{X \times Y}{100}$$

wherein $X = \%$ damage by herbicide (I) at an application amount of X kg/ha;

$Y = \%$ damage by herbicide (II) at an application amount of Y kg/ha;

$E =$ the damage to be expected from herbicides I+II at an application amount of X+Y kg/ha.

If the actual damage is greater than that calculated, the action of the active compound combination is more than additive, i.e. a synergistic effect exists. This is demonstrated with the aid of the biological examples in the following tables, the additive actions calculated from the above formula being stated in the right-hand column in parentheses after the results of the combination treatments.

TABLE 1

| Active compound | Dose g of active substance/ha | Damage in % on | | | | |
|---|---|---|---|---|---|---|
| | | Chenopodium album | Sinapis arvense | Apera spica venti | Triticum aestivum | Hordeum vulgare |
| I | 3 | 15 | 30 | 0 | 0 | 0 |
| | 4.5 | 20 | 35 | 0 | 0 | 0 |
| | 6 | 25 | 40 | 0 | 0 | 0 |
| | 9 | 30 | 65 | 10 | 0 | 0 |
| | 12 | 35 | 90 | 25 | 0 | 0 |
| IIa | 120 | 0 | 10 | 15 | 0 | 0 |
| | 180 | 0 | 15 | 25 | 0 | 0 |
| | 240 | 20 | 18 | 40 | 0 | 0 |
| | 360 | 40 | 35 | 60 | 0 | 0 |
| | 720 | 75 | 60 | 90 | 0 | 0 |
| IIb | 60 | 0 | 0 | 10 | 0 | 0 |
| | 90 | 0 | 10 | 15 | 0 | 0 |
| | 120 | 15 | 15 | 25 | 0 | 0 |
| | 180 | 25 | 25 | 40 | 0 | 0 |
| | 240 | 30 | 35 | 50 | 0 | 0 |
| | 600 | 80 | 90 | 80 | 0 | 0 |

TABLE 2

| Active compound | Dose g of active substance/ha | | Chenopodium album | Sinapis arvense | Apera spica venti | Triticum aestivum | Hordeum vulgare |
|---|---|---|---|---|---|---|---|
| I + IIa | 6 | +120 | 35 (25) | 60 (46) | 25 (15) | 0 | 0 |
| | 9 | +180 | 46 (30) | 85 (71) | 45 (33) | 0 | 0 |
| | 12 | +240 | 65 (48) | 100 (92) | 70 (55) | 0 | 0 |
| | 3 | +120 | 25 (15) | 50 (37) | 20 (15) | 0 | 0 |
| | 4.5 | +180 | 40 (20) | 60 (45) | 35 (25) | 0 | 0 |
| | 3 | +240 | 40 (32) | 60 (43) | 45 (40) | 0 | 0 |
| | 4.5 | +360 | 65 (52) | 80 (58) | 75 (60) | 0 | 0 |
| | 3 | +360 | 60 (49) | 68 (55) | 70 (60) | 0 | 0 |
| | 3 | +720 | 100 (79) | 100 (72) | 95 (90) | 0 | 0 |
| I + IIb | 6 | +60 | 35 (25) | 50 (40) | 30 (10) | 0 | 0 |
| | 9 | +90 | 45 (30) | 85 (69) | 40 (24) | 0 | 0 |
| | 12 | +120 | 60 (45) | 100 (92) | 65 (44) | 0 | 0 |
| | 3 | +60 | 25 (15) | 40 (30) | 25 (10) | 0 | 0 |
| | 4.5 | +90 | 35 (20) | 65 (42) | 38 (15) | 0 | 0 |
| | 6 | +120 | 50 (37) | 80 (49) | 60 (25) | 0 | 0 |
| | 3 | +120 | 45 (28) | 45 (41) | 55 (25) | 0 | 0 |
| | 4.5 | +180 | 55 (40) | 75 (52) | 70 (40) | 0 | 0 |
| | 6 | +240 | 70 (48) | 95 (61) | 85 (50) | 0 | 0 |
| | 3 | +240 | 60 (41) | 80 (55) | 80 (50) | 0 | 0 |
| | 3 | +600 | 100 (83) | 100 (93) | 90 (80) | 0 | 0 |

We claim:

1. An herbicidal composition which comprises 3-(4,6-dimethoxy-2-pyrimidinyl)-1-[(N-methyl-N- methylSulfonyl)-aminosulfonyl]-urea of the formula I

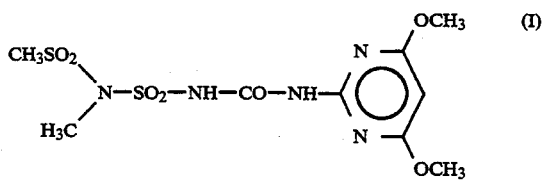

in combination with a phenylurea herbicide (II) selected from the group consisting of isoproturon and monolinuron in a weight ratio of I:II from 1:10 to 1:240.

2. An herbicidal composition as claimed in claim 1 wherein the phenylurea herbicide (II) is isoproturon and the weight ratio of I:II is from 1:20 to 1:240.

3. An herbicidal composition as claimed in claim 1 wherein the phenylurea herbicide (II) is monolinuron and the weight ratio of I:II is from 1:10 to 1:200.

4. An herbicidal composition as claimed in claim 1 which contains 2 to 95% by weight of active ingredients I and II and 98 to 5% by weight of customary formulation auxiliaries.

5. A herbicidal composition as claimed in claim 1, which contains 2-95% by weight of active compound mixture and 98-5% by weight of customary formulation auxiliaries for preparations from the group comprising wettable powders, dusting agents, granules or sprayable solutions.

6. An herbicidal composition as claimed in claim 2 which contains 2 to 95% by weight of active ingredients I and II and 98 to 5% by weight of customary formulation auxiliaries.

7. An herbicidal composition as claimed in claim 3 which contains 2 to 95% by weight of active ingredients I and II and 98 to 5% by weight of customary formulation auxiliaries.

8. A method for selectively or non-selectively controlling weeds, which comprises applying an effective amount of a synergistic mixture as defined in claim 2 to the area to be treated.

9. A method for selectively or non-selectively controlling weeds, which comprises applying an effective amount of a synergistic mixture as defined in claim 3 to the area to be treated.

* * * * *